US00PP24889P2

(12) United States Plant Patent
van den Bos

(10) Patent No.: US PP24,889 P2
(45) Date of Patent: Sep. 16, 2014

(54) *ARDISIA* PLANT NAMED 'QUEEN PABLO'

(50) Latin Name: *Ardisia crenata*
Varietal Denomination: Queen Pablo

(71) Applicant: Dick van den Bos, 's Gravenzande (NL)

(72) Inventor: Dick van den Bos, 's Gravenzande (NL)

( * ) Notice: Subject to any disclaimer, the term of this patent is extended or adjusted under 35 U.S.C. 154(b) by 91 days.

(21) Appl. No.: 13/694,151

(22) Filed: Oct. 31, 2012

(51) Int. Cl.
*A01H 5/00* (2006.01)

(52) U.S. Cl.
USPC ..... Plt./263.1

(58) Field of Classification Search
USPC ..... Plt./263.1
See application file for complete search history.

(56) References Cited

PUBLICATIONS

PLUTO Plant Variety Database 2013-06. Search for Queen Pablo plant. p. 1.*

* cited by examiner

*Primary Examiner* — Annette Para
(74) *Attorney, Agent, or Firm* — C. A. Whealy

(57) ABSTRACT

A new and distinct cultivar of *Ardisia* plant named 'Queen Pablo', characterized by its compact and broadly upright plant habit; moderately vigorous growth habit; dark green-colored leaves; freely flowering habit; and numerous creamy white-colored fruits.

4 Drawing Sheets

Botanical designation: *Ardisia crenata.*
Cultivar denomination: 'QUEEN PABLO'.

BACKGROUND OF THE INVENTION

The present invention relates to a new and distinct cultivar of *Ardisia* plant, botanically known as *Ardisia crenata* and hereinafter referred to by the name 'Queen Pablo'.

The new *Ardisia* plant is a naturally-occurring whole plant mutation of *Ardisia crenata* 'Queen Star', not patented. The new *Ardisia* plant was discovered and selected by the Inventor as a single plant from within a population of plants of 'Queen Star' in a controlled greenhouse environment in 's-Gravenzande, The Netherlands in December, 2008.

Asexual reproduction of the new *Ardisia* plant by vegetative cuttings in 's-Gravenzande, The Netherlands since December, 2008 has shown that the unique features of this new *Ardisia* plant are stable and reproduced true to type in successive generations.

SUMMARY OF THE INVENTION

Plants of the new *Ardisia* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'Queen Pablo'. These characteristics in combination distinguish 'Queen Pablo' as a new and distinct *Ardisia* plant:

1. Compact and broadly upright plant habit.
2. Moderately vigorous growth habit.
3. Dark green-colored leaves.
4. Freely flowering habit.
5. Numerous creamy white-colored fruits.

Plants of the new *Ardisia* differ primarily from plants of the parent, 'Queen Star' primarily in fruit color as plants of 'Queen Star' have red-colored fruits.

Plants of the new *Ardisia* can be compared to plants of unnamed selections of *Ardisia crenata* known to the Inventor. In side-by-side comparisons, conducted in 's-Gravenzande, The Netherlands, plants of the new *Ardisia* differed primarily from plants of the unnamed selections in the following characteristics:

1. Plants of the new *Ardisia* were more compact and denser than plants of the unnamed selections.
2. Plants of the new *Ardisia* developed basal sprouts whereas plants of the unnamed selections did not develop basal sprouts.

BRIEF DESCRIPTION OF THE PHOTOGRAPHS

The accompanying colored photographs illustrate the overall appearance of the new *Ardisia* plant showing the colors as true as it is reasonably possible to obtain in colored reproductions of this type. Colors in the photographs may differ slightly from the color values cited in the detailed botanical description which accurately describe the actual colors of the new *Ardisia* plant.

The photograph on the first sheet comprises a side perspective view of a typical flowering plant of 'Queen Pablo' grown in a container.

The photograph on the second sheet is a close-up view of typical flower buds and flowers of 'Queen Pablo'.

The photograph on the third sheet comprises a side perspective view of a typical plant of 'Queen Pablo' with developing fruits.

The photograph on the fourth sheet is a close-up view of typical developed fruits of 'Queen Pablo'.

DETAILED BOTANICAL DESCRIPTION

Plants used for the aforementioned photographs and following description were grown in 1.5-liter containers during the late spring and summer in a glass-covered greenhouse in 's-Gravenzande, The Netherlands and under cultural practices which closely approximate commercial *Ardisia* production. During the production of the plants, day temperatures ranged from 19° C. to 23° C. and night temperatures ranged from 16° C. to averaged 20° C. Plants were 1.5 years old when the photographs and description were taken. In the following description, color references are made to The Royal Horticultural Society Colour Chart, 2007 Edition, except where general terms of ordinary dictionary significance are used.

Botanical classification: *Ardisia crenata* 'Queen Pablo'.

Parentage: Naturally-occurring whole plant mutation of *Ardisia crenata* 'Queen Star', not patented.

Propagation:

*Type cutting*.—Vegetative cuttings.

*Time to initiate roots, summer*.—About 60 days at soil temperatures about 25° C. and ambient temperatures, about 20° C.

*Time to initiate roots, winter*.—About 90 days at soil temperatures about 25° C. and ambient temperatures about 20° C.

*Time to produce a rooted young plant, summer*.—About 90 days at soil temperatures about 25° C. and ambient temperatures about 20° C.

*Time to produce a rooted young plant, winter*.—About 140 days at soil temperatures about 25° C. and ambient temperatures about 20° C.

*Root description*.—Medium in thickness; fleshy; brown in color.

*Rooting habit*.—Moderately freely branching; medium density.

Plant description:

*Plant and growth habit*.—Perennial evergreen shrub; compact and broadly upright plant habit; dense and bushy appearance; moderately vigorous growth habit.

*Branching habit*.—Freely basally branching habit with about 30 lateral branches developing per plant.

*Plant height*.—About 30 cm.

*Plant width (spread)*.—About 28 cm.

*Lateral branch description*.—Length: About 7.7 cm. Diameter: About 2 mm. Internode length: About 3 mm. Strength: Strong. Aspect: About 50° from the main stem. Texture: Smooth, glabrous. Color: Close to 144B. Lenticels: Occurrence: Dense. Length: About 0.5 mm. Width: About 0.1 mm. Color: Close to 197A.

Foliage description:

*Arrangement*.—Alternate, simple.

*Length*.—About 8.5 cm.

*Width*.—About 3 cm.

*Shape*.—Elliptic; slightly carinate.

*Apex*.—Bluntly acuminate.

*Base*.—Attenuate.

*Margin*.—Shallowly crenulate, undulate.

*Texture, upper and lower surfaces*.—Smooth, glabrous.

*Venation pattern*.—Pinnate.

*Color*.—Developing leaves, upper surface: Close to 144A. Developing leaves, lower surface: Between 144B and 146D. Fully expanded leaves, upper surface: Darker than between 139A and 147A; venation, close to 143A. Fully expanded leaves, lower surface: Close to 147B; venation, close to 144C.

*Petiole length*.—About 6 mm.

*Petiole width*.—About 2 mm.

*Petiole color, upper and lower surfaces*.—Close to 144B.

Flower description:

*Flower arrangement and shape*.—Single rotate flowers arranged in terminal and axillary umbels; freely flowering habit with about 14 flowers per inflorescence and about 2,000 flowers developing per plant; flowers face slightly outwardly to drooping.

*Fragrance*.—None detected.

*Natural flowering season*.—Plants flower continuously from late spring into the summer in The Netherlands; plants begin flowering about eight months after planting.

*Flower longevity*.—Flowers last about a week on the plant; flowers not persistent.

*Flower buds*.—Length: About 5 mm. Diameter: About 3 mm. Shape: Ovate. Color: Close to 155D with small dots, close to 176C.

*Inflorescence size*.—Height: About 1.5 cm. Diameter: About 2.9 cm.

*Flowers*.—Diameter: About 1.1 cm. Depth (height): About 5 mm.

*Petals*.—Quantity and arrangement: Five in a single whorl fused at the base. Length: About 6 mm. Width: About 3 mm. Shape: Ovate. Apex: Acute. Margin: Entire. Texture, upper and lower surfaces: Smooth, glabrous. Color: When opening, upper and lower surfaces: Close to NN155B with small dots, close to 176C. Fully opened, upper and lower surfaces: Close to NN155B with small dots, close to 175B; color does not change with development.

*Sepals*.—Quantity and arrangement: Five in a single whorl fused at the base. Length: About 2 mm. Width: About 1.5 mm. Shape: Ovate. Apex: Acute. Margin: Entire. Texture, upper and lower surfaces: Smooth, glabrous. Color: When opening, upper and lower surfaces: Close to NN155B with small dots, close to 176C. Fully opened, upper and lower surfaces: Close to NN155B with small dots, close to 175B; color does not change with development.

*Peduncles*.—Length: About 2.7 cm. Diameter: About 1.5 mm. Strength: Strong. Aspect: Terminal inflorescences, erect; axillary inflorescences, about 50° from main stem. Texture: Smooth, glabrous. Color: Close to 144A. Lenticels: Occurrence: Moderately dense. Length: About 0.4 mm. Width: About 0.1 mm. Color: Close to 197A.

*Pedicels*.—Length: About 9 mm. Diameter: About 0.75 mm. Strength: Moderately strong. Aspect: About 10° to 70° from peduncle. Texture: Smooth, glabrous. Color: Close to 144B. Lenticels: Occurrence: Moderately dense. Length: About 0.3 mm. Width: About 0.1 mm. Color: Close to 197A.

*Reproductive organs*.—Stamens: Quantity per flower: About five. Anther shape: Narrowly deltoid. Anther length: About 3 mm. Anther color: Close to 13B with dots, close to N199A. Pollen amount: Moderate. Pollen color: Close to 11C. Pistils: Quantity per flower: One. Pistil length: About 4 mm. Stigma shape: Club-shaped. Stigma color: Close to 144C. Style length: About 3 mm. Style color: Close to 157D. Ovary color: Close to 144A to 144B.

*Fruits*.—Length: About 7 mm Diameter: About 8 mm. Shape: Spherical. Texture: Smooth, glabrous. Color, when developing: Close to N144B. Color, fully developed: Close to 158C to 158D.

*Seeds*.—Length: About 5 mm. Diameter: About 5 mm. Color: Close to 159A.

Disease & pest resistance: Plants of the new *Ardisia* have not been observed to be resistant to pathogens and pests common to *Ardisia* plants.

Weather & temperature tolerance: Plants of the new *Ardisia* have been observed to tolerate wind, rain and temperatures ranging from about 5° C. to about 35° C.

It is claimed:

1. A new and distinct *Ardisia* plant named 'Queen Pablo' as illustrated and described.

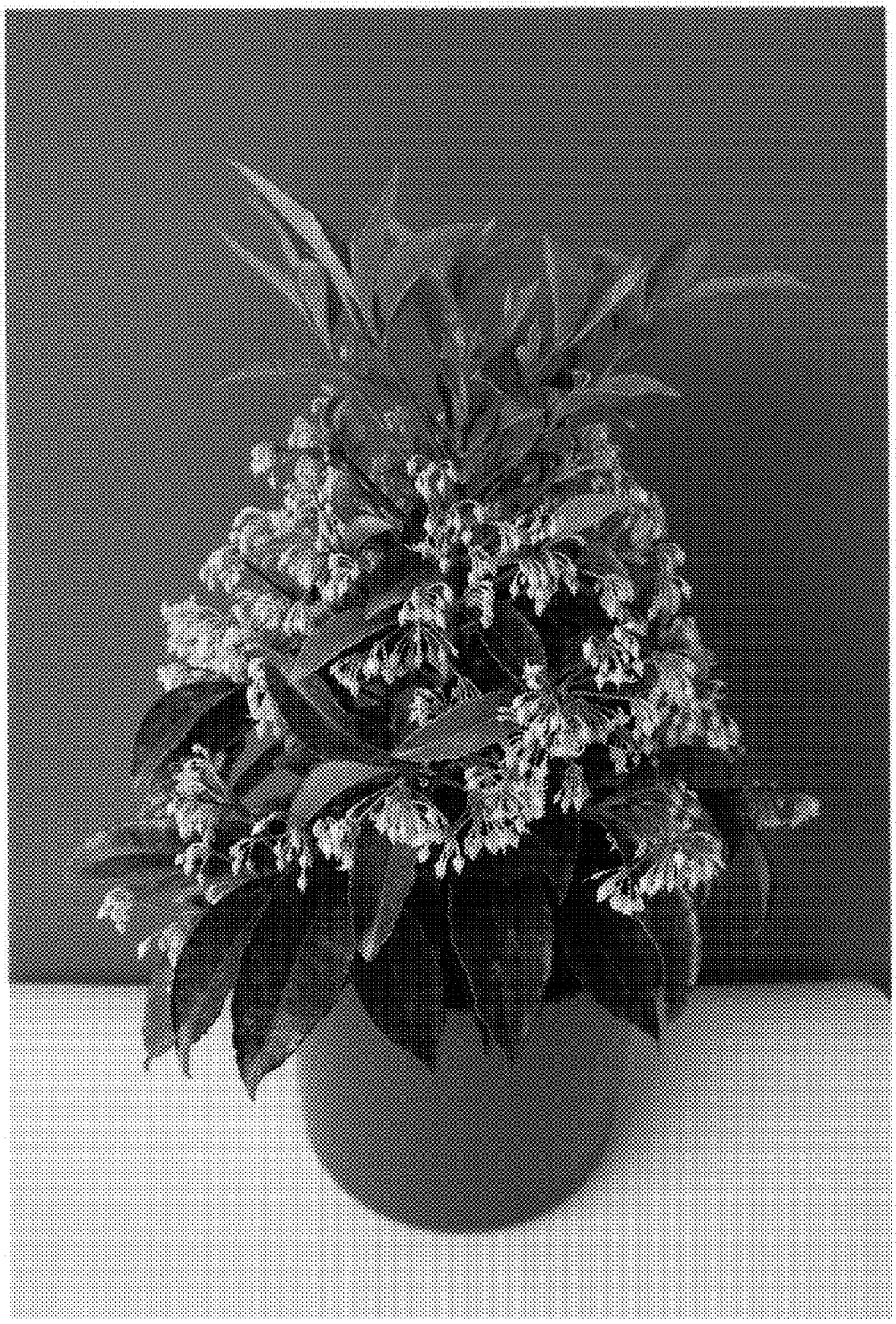

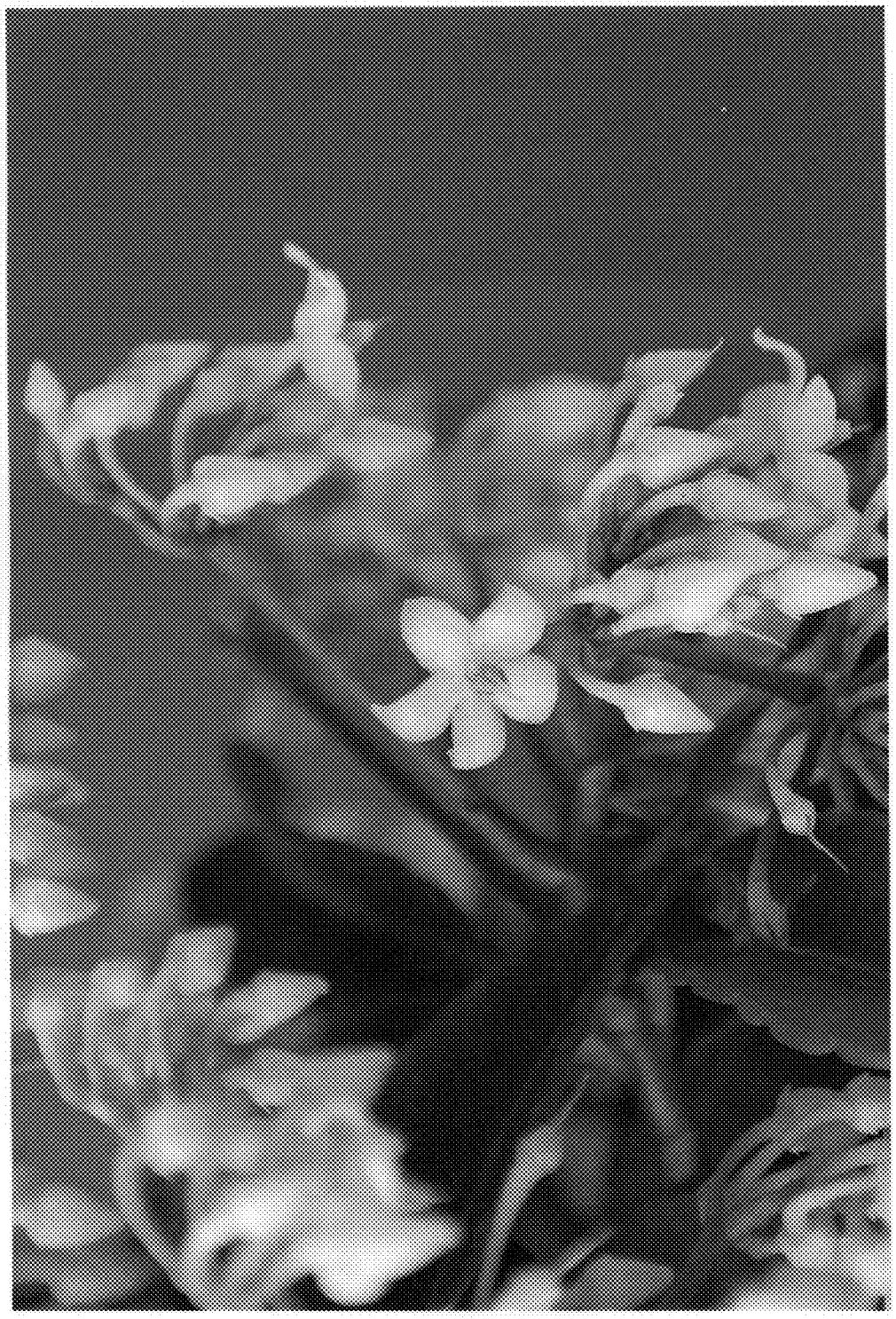

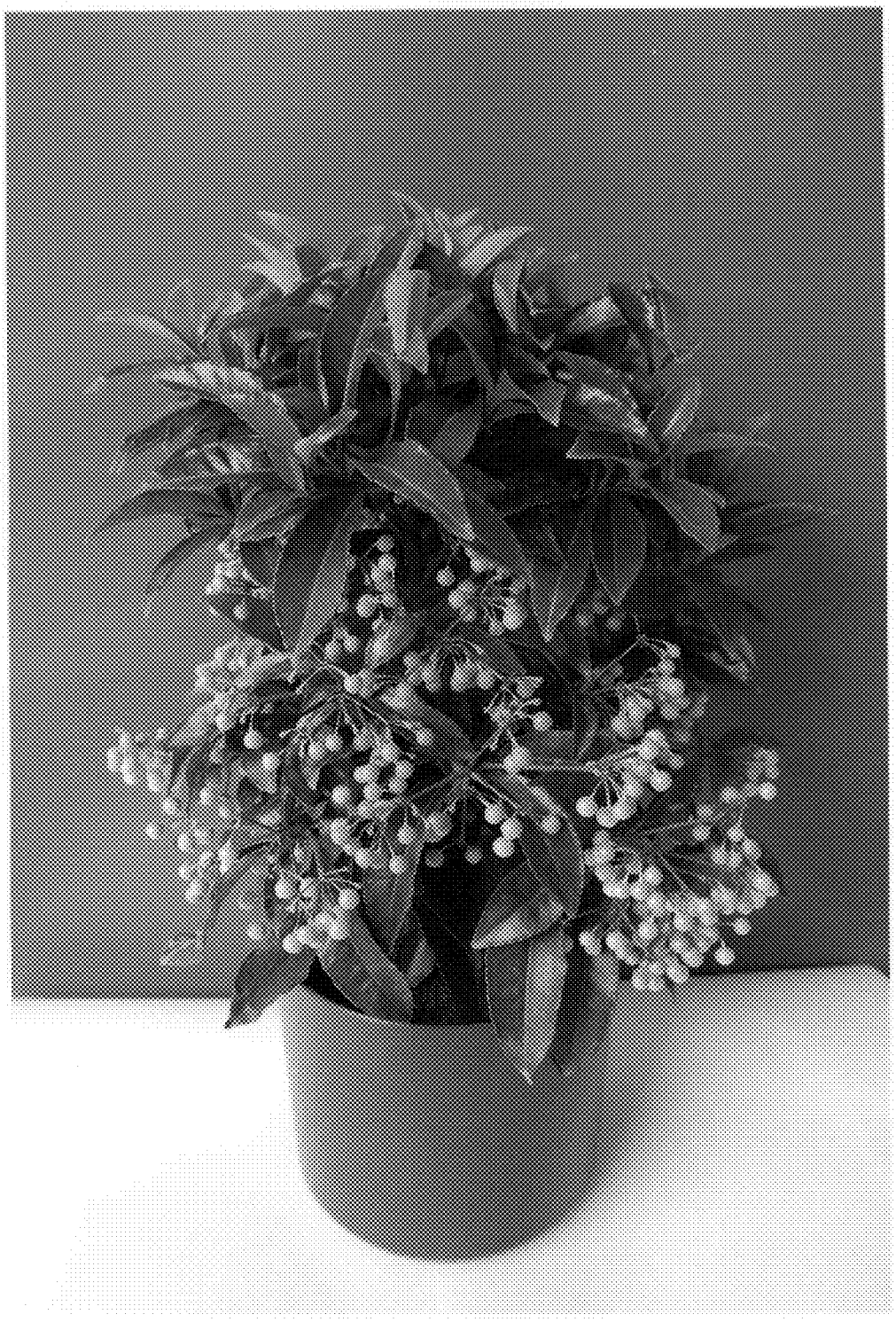

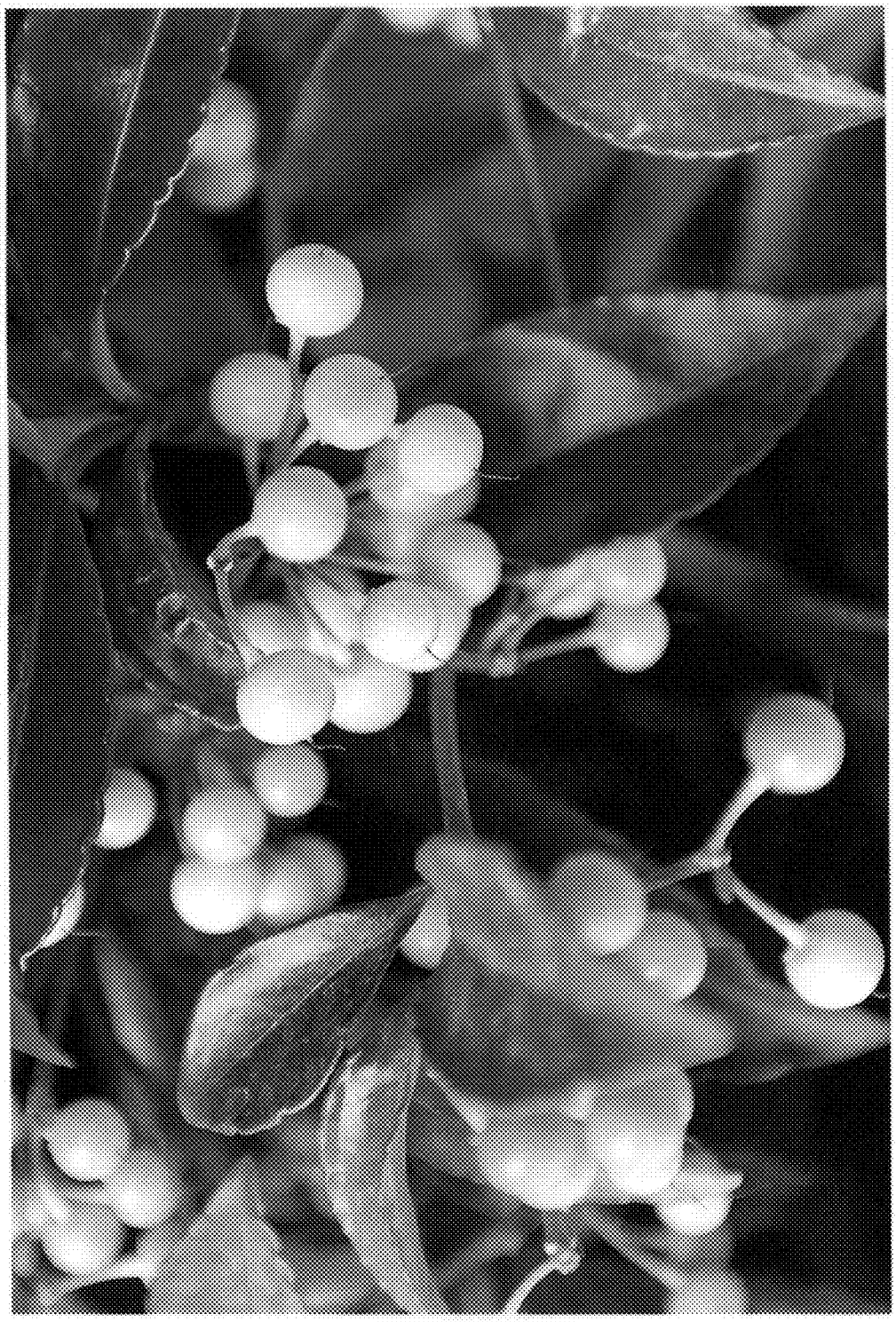

* * * * *